United States Patent
Ramadhyani et al.

(10) Patent No.: US 9,078,733 B2
(45) Date of Patent: Jul. 14, 2015

(54) CLOSED-LOOP SYSTEM FOR CRYOSURGERY

(75) Inventors: Satish Ramadhyani, Minneapolis, MN (US); Ted J. Perron, White Bear Lake, MN (US); Mark Zagarola, Lebanon, NH (US); Vineel Vallapureddy, Coon Rapids, MN (US)

(73) Assignee: Galil Medical Inc., Arden Hills, MN (US)

( * ) Notice: Subject to any disclaimer, the term of this patent is extended or adjusted under 35 U.S.C. 154(b) by 334 days.

(21) Appl. No.: 13/569,822

(22) Filed: Aug. 8, 2012

(65) Prior Publication Data
US 2014/0046312 A1 Feb. 13, 2014

(51) Int. Cl.
*A61B 18/02* (2006.01)
*A61F 7/00* (2006.01)

(52) U.S. Cl.
CPC .............. *A61F 7/0085* (2013.01); *A61B 18/02* (2013.01); *A61B 2018/0262* (2013.01); *A61B 2018/0293* (2013.01); *A61F 2007/0056* (2013.01); *A61F 2007/0057* (2013.01)

(58) Field of Classification Search
None
See application file for complete search history.

(56) References Cited

U.S. PATENT DOCUMENTS

| | | | |
|---|---|---|---|
| 3,351,063 A | 11/1967 | Malaker et al. | |
| 5,590,538 A * | 1/1997 | Hsu et al. | 62/51.2 |
| 6,019,783 A | 2/2000 | Philips et al. | |
| 7,381,208 B2 | 6/2008 | van der Walt et al. | |
| 7,500,973 B2 | 3/2009 | Vancelette et al. | |
| 2007/0225781 A1* | 9/2007 | Saadat et al. | 607/105 |
| 2008/0027419 A1* | 1/2008 | Hamel et al. | 606/20 |
| 2008/0114344 A1 | 5/2008 | Xiao et al. | |
| 2008/0125764 A1* | 5/2008 | Vancelette et al. | 606/22 |
| 2008/0200910 A1* | 8/2008 | Burger et al. | 606/20 |
| 2009/0270851 A1 | 10/2009 | Babkin et al. | |
| 2011/0306958 A1* | 12/2011 | Berzak et al. | 606/24 |
| 2012/0059364 A1 | 3/2012 | Baust et al. | |
| 2012/0109119 A1* | 5/2012 | Lalonde | 606/23 |
| 2012/0158103 A1 | 6/2012 | Bledsoe | |

FOREIGN PATENT DOCUMENTS

| | | |
|---|---|---|
| WO | 92/04872 A1 | 4/1992 |
| WO | 2007/109656 A2 | 9/2007 |
| WO | WO2012058430 A2 | 5/2012 |

OTHER PUBLICATIONS

Invitation to Pay Additional Fees and Partial International Search Report for Application No. PCT/US2013/054046 dated Jan. 2, 2014, 8 pages.

(Continued)

*Primary Examiner* — Brian T Gedeon
*Assistant Examiner* — Ankit Tejani
(74) *Attorney, Agent, or Firm* — Fredrikson & Byron, P.A.

(57) ABSTRACT

A closed-loop system for cryosurgery includes a cryofluid at cryogenic temperatures flowing through a closed-loop flow path. A pump, configured for operating at cryogenic temperatures, circulates the cryofluid in the closed-loop flow path. The closed-loop flow path includes a heat exchanger coupled to a heat sink configured for cooling the cryofluid in the closed-loop flow path to cryogenic temperatures. The closed-loop system includes one or more cryoneedles configured for providing cryotherapy, and one or more flow control devices, wherein each flow control device is configured for operating at cryogenic temperature and for selectively flow connecting or flow disconnecting at least one of the cryoneedles to the closed-loop flow path.

30 Claims, 5 Drawing Sheets

(56) References Cited

OTHER PUBLICATIONS

International Search Report and Written Opinion for International Application No. PCT/US2013/054046, Jun. 18, 2014, 21 pages.
Fredrickson, Kylie, et al. "A design method for mixed gas Joule-Thomson refrigeration cryosurgical probes", International Journal of Refrigeration 29 (2006) 700-715, available online Feb. 17, 2006 at www.sciencedirect.com.
Skye, H.M., et al., "Modeling, Optimization, and Experimentation with a Two Stage Mixed Gas Cascade Joule Thomson Cryoprobe", ASHRAE Progress Report, 23 pages, Jun. 2008.
Skye, H.M., et al., "Modeling and Optimization of a Two-Stage Mixed-Gas Joule-Thomson Cryoprobe System", University of Wisconsin—Madison, Cryocoolers 15, pp. 415-424, International Cryocooler Conference, Inc., Boulder, Colorado, 2009.
Website: http://www.coopersurgical.com/ourproducts/cryoablation/heroption/Pages/csland.aspx?LC=Her%20Option.

* cited by examiner

CLOSED-LOOP SYSTEM FOR CRYOSURGERY

TECHNICAL FIELD

The present invention relates to cryosurgical systems for providing cryotherapy. In particular, the invention pertains to a closed-loop system for cryosurgery.

BACKGROUND

Most cryosurgical systems are open-loop systems in that the cryofluid, typically Argon and/or Nitrogen, used for providing cryotherapy flows from a reservoir, e.g., a tank, under a relatively high pressure, through the one or more cryoneedles being used for providing cryotherapy, and is thereafter exhausted or purged to the surrounding environment. As such, continuous use of the system depletes the reservoir which must then be replaced. Also, substantial pressure drops across various components is an inherent characteristic of prior art open-loop systems. Therefore, it becomes necessary to ensure that the reservoir contains at least a sufficient amount of the cryofluid for completing a cryosurgical procedure without interruptions for replacing the reservoir. Accordingly, it is not uncommon to have one or more extra reservoirs on hand and ready for use if and when necessary. Often times, a partially depleted reservoir is replaced with a fully-charged tank prior to starting a procedure. As can be seen, exhausting the cryofluid from the cryoneedles after use and replacement of partially discharged reservoirs result in both waste and an increase in the cost of a cryosurgical procedure.

To the extent that closed-loop cryosurgical systems have been developed, such systems have limitations that render them unsuitable for many cryosurgical applications.

Accordingly, there exists a need for closed-loop systems for cryosurgery wherein the cryofluid is re-circulated for re-use and not deliberately exhausted after a single use, and wherein the pressure drops across the various components is minimized such that the nominal pressure throughout the closed-loop flow path is substantially less than that in prior art open-loop systems.

SUMMARY

In accordance with an embodiment of the invention, a closed-loop system for cryosurgery includes a cryofluid at cryogenic temperatures flowing through a closed-loop flow path having a nominal pressure throughout and at cryogen temperature throughout. A pump, configured for operating at cryogenic temperatures, circulates the cryofluid in the closed-loop flow path. The closed-loop flow path includes a heat exchanger coupled to a heat sink for cooling the cryofluid in the closed-loop flow path to cryogenic temperatures. The closed-loop system includes one or more cryoneedles for providing cryotherapy, and one or more flow control devices, wherein each flow control device is configured for operating at cryogenic temperature and for selectively flow connecting or flow disconnecting at least one of the cryoneedles to the closed-loop flow path. Connecting a cryoneedle to the closed-loop flow path enables the flow of the cryofluid at cryogenic temperatures into and through the flow connected cryoneedle, thereby providing cryotherapy. Disconnecting a cryoneedle from the closed-loop flow path disables the flow of the cryofluid into and through the cryoneedle, thereby stopping the cryotherapy.

Some embodiments of the closed-loop system include a cryofluid reservoir intended for pressurizing the closed-loop flow path and/or for flushing the cryoneedles flow connected to the flow path. In some embodiments of the closed-loop system, the closed-loop flow path includes two or more heat exchangers, wherein each one of the two or more heat exchangers is coupled to a heat sink configured for cooling the cryofluid in the closed-loop flow path to cryogenic temperatures.

An alternate embodiment of the closed-loop system includes a recuperator in the closed-loop flow path configured for transferring thermal energy between a first section of the flow path operating at cryogenic temperature and a second section of the flow path operating at temperatures substantially greater than the cryogenic temperatures. In some embodiments of the closed-loop system, the pump is configured for operating at temperatures substantially greater than the cryogenic temperatures, and is therefore positioned in the second section of the closed-loop flow path. In other embodiments of the closed-loop system, the one or more flow control devices are configured for operating at temperatures substantially greater than the cryogenic temperatures, and are therefore also positioned in the second section of the closed-loop flow path.

DETAILED DESCRIPTION

While multiple embodiments are disclosed herein, still others may become apparent to one skilled in the art. In the following, certain illustrative and non-limiting embodiments are described in detail with reference to the accompanying drawings wherein like elements are designated by like numerals. It should be clearly understood that there is no intent, implied or otherwise, to limit the invention in any form or manner to that described herein. As such, all alternative embodiments are considered as falling within the spirit, scope and intent of the disclosure. The metes and bounds of the invention are defined by the appended claims and any and all equivalents thereof.

Figure 1:
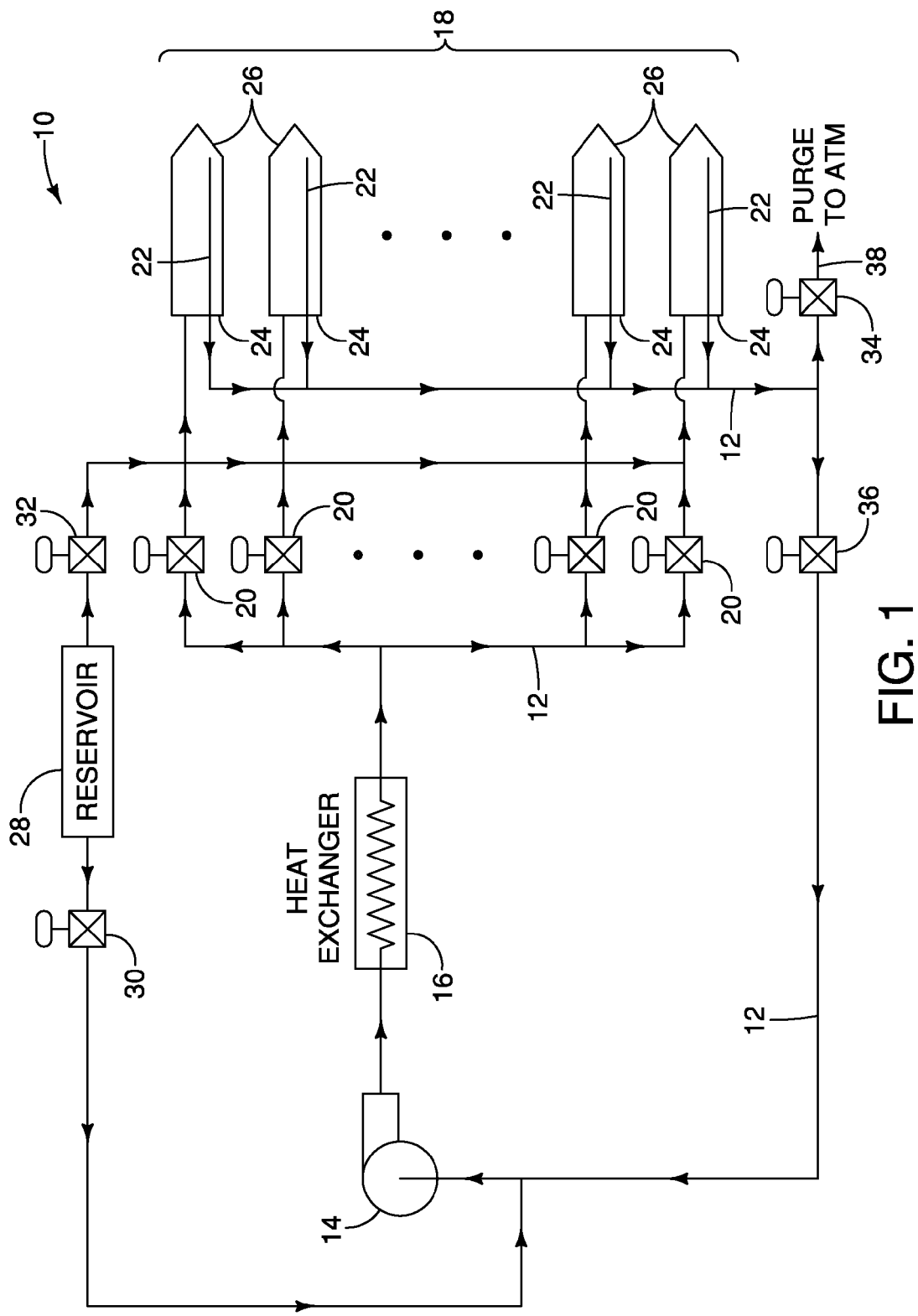
FIG. 1 illustrates an embodiment of a closed-loop system for cryosurgery.

FIG. 1 illustrates an embodiment of closed-loop system 10 for cryosurgery. System 10 includes closed-loop flow path 12 within which a cryofluid flows at cryogenic temperatures. In some embodiments of closed-loop system 10, the cryofluid is a compressed cryogas such as nitrogen or argon. Pump 14 circulates the cryofluid in flow path 12, and heat exchanger 16 cools the cryogenic fluid in flow path 12. System 10 includes one or more cryoneedles 18 in flow path 12, wherein each cryoneedle 18 is configured for providing a cryotherapy to a tissue in which it is inserted. Flow path 12 includes one or more flow control devices 20, wherein each flow control device 20 is configured for selectively flow connecting or flow disconnecting one or more cryoneedles 18. Accordingly, operating flow control devices 20 to flow connect cryoneedles 18 to flow path 12 enables the cryofluid at cryogenic temperatures in flow path 12 to flow through cryoneedles 18 and provide cryotherapy. The cryofluid flowing through and exiting cryoneedles 18 is returned to flow path 12. Similarly, operating flow control devices 20 to flow disconnect one or more cryoneedles 18 from flow path 12 disables the flow of the cryofluid at cryogenic temperatures in flow path 12 through cryoneedles 18 and thereby stops the cryosurgical procedure.

It will be apparent to one skilled in the art that the pressure in flow path 12 will decrease as the cryofluid at cryogenic temperatures flows through the plumbing and the various components of system 10 such as for example heat exchanger 16, cryoneedles 18, flow control devices 20, etc. Accordingly, pump 14 is configured for circulating cryofluid at cryogenic temperatures to compensate for such pressure drops in flow path 12, and maintain the cryofluid (e.g., compressed gas such as nitrogen or argon) in flow path 12 within a predefined range (or variance) about a predetermined nominal pressure. In a non-limiting exemplary embodiment, pump 14 circulates the cryofluid at cryogenic temperatures in flow path 12 at a flow rate ranging between approximately 0.1 liters/minute and approximately 0.8 liters/minute and at a nominal pressure of approximately 10MPa with a variance of approximately ±0.5 MPa. Some embodiments of pump 14 are constant flow pumps configured to maintain the cryofluid flow rate within a relatively narrow predefined range. Other embodiments of pump 14 are variable flow pumps configured to accommodate cryofluid flow rates over a relatively wide predefined range.

It will be also apparent to one skilled in the art that the temperature of the cryofluid will increase as the cryofluid flows through the plumbing and the various components of system 10. For example, when one or more cryoneedles 18 are flow connected to flow path 12, the temperature of the cryofluid flowing through each cryoneedle 18 will increase because of the heat gain from the tissue (or other environment) surrounding cryoneedle 18. As such, the temperature of the cryofluid exiting cryoneedles 18 will be relatively higher than that of the cryofluid entering cryoneedles 18. The temperature of the cryofluid flowing through pump 14 will also increase because of heat gain from the motor of pump 14. Accordingly, heat exchanger 16 is configured to compensate for such heat gains, and cool the cryofluid to within a predefined range (or variance) about a predetermined nominal temperature. In a non-limiting exemplary embodiment of system 10, heat exchanger 16 is coupled to a heat sink configured for extracting between approximately 100 watts and approximately 500 watts of thermal energy from the cryofluid flowing through heat exchanger 16 and cooling the cryofluid from approximately 150° K to approximately 110° K.

In a non-limiting exemplary embodiment, the heat sink is a cryogenic dewar and/or a cryocooler. Cryogenic dewars, as are well known in the art, include a flask or a vacuum flask (i.e., a dewar) configured for holding or storing a cryogen such as liquid nitrogen, liquid oxygen, liquid helium, liquid hydrogen, etc. Cryocoolers, as are also well known in the art, include Stirling-type cooler, pulse-tube refrigerator (PTR), Gifford-McMahon (GM) cooler, Joule-Thomson (JT) cooler, etc.

In some embodiments of system 10, one or more cryoneedles 18 are substantially similar in size (e.g., length, diameter, etc.), material, etc. as conventional prior art cryoneedles as are well known in the art. However, certain embodiments of cryoneedles 18 differ from the prior art cryoneedles in that cryoneedles 18 do not include a JT cooler. Generally, cryoneedles 18 include lumen 22 therewithin extending from proximal end 24 to a location proximate distal end 26 of cryoneedle 18. As such, cryoneedle 18 includes an annular space extending between proximal and distal ends 24 and 26 and defined at least in part by the space between an inside surface of cryoneedle 18 and an outside surface of lumen 22. When cryoneedle 18 is flow connected to flow path 12, the cryofluid at cryogenic temperatures enters the annular space inside cryoneedle 18 through an inlet port at proximal end 24 of cryoneedle 18 and flows through the annular space from proximal end 24 to distal end 26. The cryofluid then flows through lumen 22 from distal end 26 to proximal end 24, and exits cryoneedle 18 through an exit port of lumen 22 at proximal end 24 of cryoneedle 18. The cryofluid exiting cryoneedle 18 is returned back to flow path 12.

In some embodiments of system 10, one or more flow control devices 20 comprise one or more embodiments configured for operating at cryogenic temperatures of the cryofluid in flow path 12. Some embodiments of flow control devices 20 have two operating states including a fully-open state and a fully-closed state. When flow control device 20 is in the fully-open state, cryoneedle 18 is flow connected to flow path 12 for enabling the flow of the cryofluid at cryogenic temperatures into, and through, cryoneedle 18. When flow control device 20 is in the fully-closed state, cryoneedle 18 is flow disconnected from flow path 12 for disabling the flow of the cryofluid at cryogenic temperatures into, and through, cryoneedle 18. Other embodiments of flow control devices 20 are further operable to vary the flow rate of the cryofluid flowing therethrough, and into and through cryoneedle 18.

In operation, pump 14 circulates the cryofluid at cryogenic temperatures within flow path 12. One or more flow control devices 20 are operated to flow connect or flow disconnect one or more cryoneedles 18 to flow path 12. As described herein above, flow control devices 20, when in the fully-closed state, flow disconnect cryoneedles 18 from flow path 12 and disable the flow of the cryofluid through cryoneedle 18. When transitioning between the fully-open and the fully closed state and/or when in the fully-open state, flow control devices 20 flow connect cryoneedles 18 to flow path 12 and enable the flow of the cryofluid at cryogenic temperatures through cryoneedles 18. In some embodiments of system 10, at least one of one or more flow control devices 20 is associated with at least one of one or more cryoneedles 18, which association enables or disables the flow of the cryofluid through the at least one cryoneedle 18 by respectively flow connecting or flow disconnecting flow path 12 to the at least one cryoneedle 18.

Embodiments of system 10, such as that illustrated in FIG. 1, include cryofluid reservoir 28, and flow control devices 30, 32, 34 and 36 configured for selectively charging and/or pressurizing flow path 12, and for flushing one or more cryoneedles 18. During normal operation, i.e., when system 10 is operated for providing cryotherapy, one or more flow control devices 20 are operated to flow connect one or more cryoneedles 18 to flow path 12, flow control devices 32 and 34 are placed in a fully-closed state, and flow control devices 30 and 36 are placed in a fully-open state such that pump 14 circulates the cryofluid within flow path 12 and the flow connected cryoneedles 18.

It will be apparent to one skilled in the art that the volume (and pressure) of the cryofluid within flow path 12 will decrease when heat exchanger 16 cools the cryofluid. Accordingly, with flow control device 30 placed in the fully-open state, cryofluid from reservoir 28 will be added into flow path 12 to compensate for the decrease in the volume of the cryofluid within flow path 12, and for maintaining the nominal pressure with flow path 12. Also, while closed-loop flow path 12 is hermetically sealed, at least some leakage of the cryofluid through the numerous joints and connectors is contemplated in some embodiments of system 10. Such leakage of the cryofluid is compensated for by the addition of the cryofluid from reservoir 28 into flow path 12 through the fully-open flow control device 30.

FIG. 1 illustrates an embodiment of system 10 wherein one or more cryoneedles 18 flow connected to flow path 12 are downstream of heat exchanger 16 and upstream of pump 14, and heat exchanger 16 is downstream of pump 14. As such, flow path 12 is defined at least partially by serial fluid communication between pump 14 and heat exchanger 16. The cryofluid exiting pump 14 flows into and through heat exchanger 16. Upon exiting heat exchanger 16, flow path 12 separates or diverges into one or more parallel flow paths providing parallel fluid communication between heat exchanger 16 and one or more flow control devices 20. Each one of one or more flow control device 20 is in serial fluid communication with at least one of one or more cryoneedles 18. One or more flow control devices 20 enable or disable the flow of the cryofluid from heat exchanger 16 through at least one of one or more cryoneedles 18. One or more cryoneedles 18 are in parallel fluid communication with pump 14 such that upon exiting one or more cryoneedles 18, the cryofluid combines or converges into a single flow path to pump 14.

As will be appreciated by one skilled in the art, prior to using system 10 for a cryosurgical procedure and/or when a new cryoneedle 18 is attached to at least one of one or more flow control devices 20 during a cryosurgical procedure, it is desirable and/or advantageous to flush and/or purge any fluid from within cryoneedles 18 prior to flow connecting one or more cryoneedles 18 to flow path 12. It will be evident that if cryoneedles 18 are not flushed, then any fluid therewithin will enter flow path 12 and mix with the cryofluid flowing therethrough. The process for flushing cryoneedles 18, in accordance with one non-limiting exemplary embodiment, includes turning off pump 14 to stop the flow of the cryofluid through flow path 12 and placing each of one or more flow control devices 20, 30 and 36 in a fully-closed state. Next, one or more cryoneedles 18 are attached to one or more flow control devices 20. Then, flow control devices 32 and 34 are transitioned from the fully-closed state to the fully-open state such that the cryofluid from reservoir 28 enters and flows through cryoneedles 18. The cryofluid exiting cryoneedles 18 flows through flow control device 34 and is purged or discharged along flow path 38 into the surrounding atmosphere. After a predetermined amount of time or when it is determined that cryoneedles 18 have flushed, flow control device 34 is placed in the fully-closed state before also placing flow control device 32 in the fully-closed state. Next, flow control devices 30 and 36 are placed in the fully-open state. Then, pump 14 is started for circulating the cryofluid in flow path 12 and one or more flow control devices 20 are operated as desired for enabling or disabling the flow of the cryofluid between one or more cryoneedles 18 and flow path 12.

In some embodiments of system 10, cryoneedles 18 are pre-conditioned during and/or after manufacture such that it is not necessary to flush them prior to their use. In a non-limiting exemplary embodiment, cryoneedles 18 are first flushed and then charged with the cryofluid during manufacture. Alternately, the flushing and/or the charging can be performed in an operating room just prior to attaching (or connecting) cryoneedle 18 to flow control device 20 by connecting cryoneedle 18 to a flush valve on a cryofluid reservoir not connected to the closed-loop cryosurgical system, opening the flush valve to permit the cryofluid to flow from the reservoir, through the cryoneedle, and purging the cryofluid to the atmosphere. Disconnecting cryoneedle 18 from the flush valve on the cryofluid reservoir will seal the cryofluid within cryoneedle 18. Such pre-charged cryoneedles 18 can then be attached to flow control device 20 for being flow connected to flow path 12 without the need for flushing prior to their use. Alternately, as described herein below with reference to FIG. 2, closed-loop system 10 can be configured for flushing and/or conditioning cryoneedle 18 prior to attaching it to flow control device 20.

Figure 2:
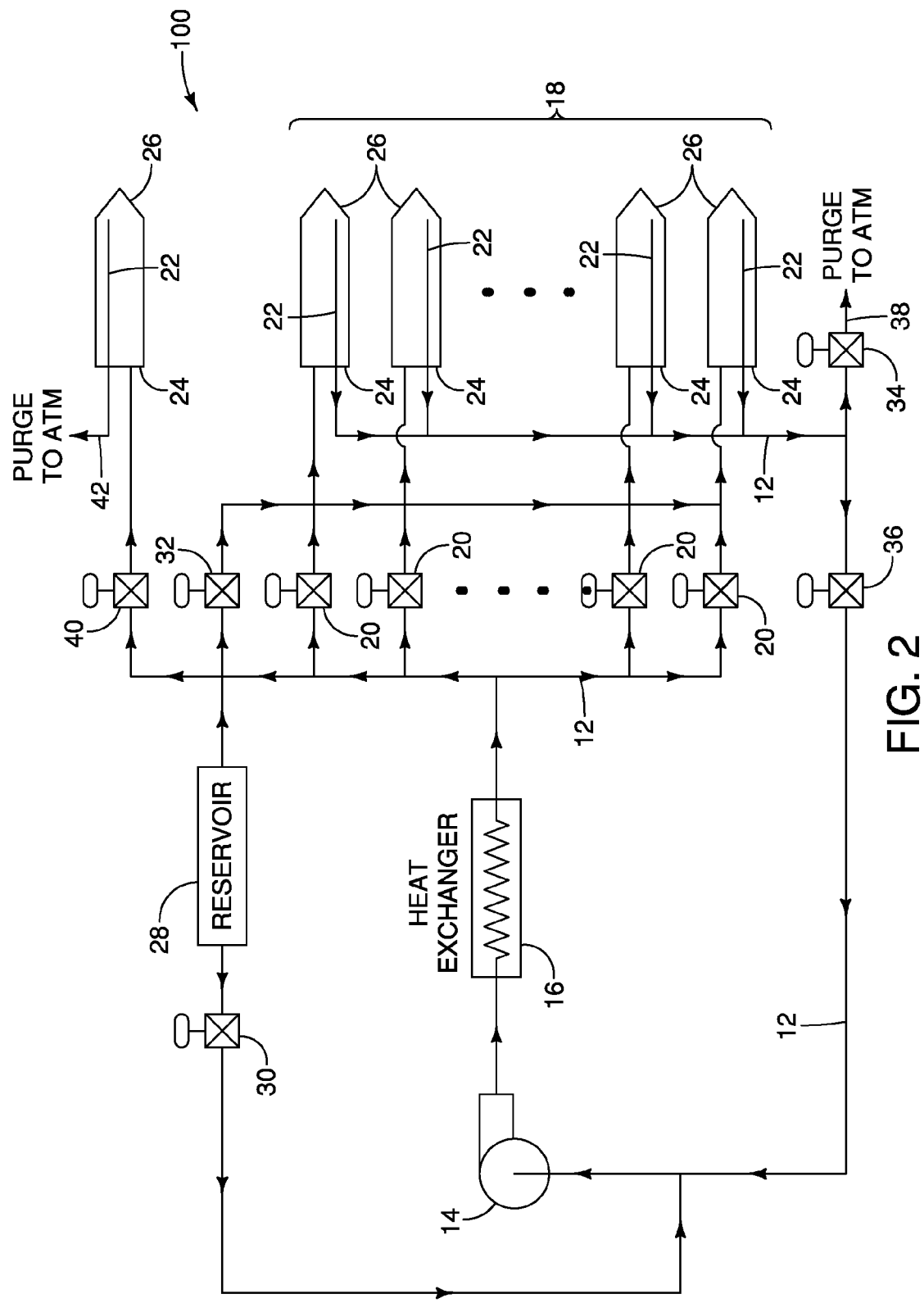
FIG. 2 illustrates an alternate embodiment of a closed-loop system for cryosurgery.

FIG. 2 illustrates an embodiment of closed-loop system 100 configured for flushing and/or conditioning cryoneedles 18 prior to their use in a cryosurgical procedure. System 100 further includes flush valve 40 in fluid communication with reservoir 28 and configured for attaching (or connecting) cryoneedle 18 thereto. Generally, flush valve 40 will be in a fully-closed state. Before attaching a cryoneedle to flow control device 20, it is first attached to flush valve 40 which is then placed in a fully-open state. As such, the cryofluid from reservoir 28 enters and flows through the cryoneedle, and thereafter purged or discharged along flow path 42 into the surrounding atmosphere. After a predetermined amount of time or when it is determined that the cryoneedle is flushed, flush valve 40 is placed in the fully-closed state. The cryoneedle is disconnected from flush valve 40 and attached to one of flow control devices 20 for use in providing cryotherapy.

In view of the foregoing, it will be evident that both closed-loop systems 10 and 100 are configured for concurrently flushing all cryoneedles 18 that are attached (or connected) to their respective flow control devices 20. As will be apparent to one skilled in the art, this will be the most likely state at the start of a cryosurgical procedure. For some cryosurgical procedures, the total number of cryoneedles that will be required for completing the procedure may have been connected to flow control devices 20 before starting the procedure, and it may not be necessary to connect additional cryoneedles during the procedure. However, during a cryosurgical procedure, it may sometimes be determined that additional cryoneedles are required for completing the procedure. For such instances, one or more pre-charged cryoneedles can be attached (or connected) to flow control devices 20 of systems 10 and 100 during the procedure, and be used without requiring further conditioning. However, if the cryoneedles have not been pre-conditioned and/or pre-charged, they may be attached to flow control devices 20 of closed-loop system 100 after they have flushed and charged as described herein above with reference to FIG. 2.

In another non-limiting exemplary embodiment, cryoneedles 18, during manufacture, are first flushed, then evacuated to create a vacuum therewithin, and thereafter sealed. Alternately, this same process can be performed in an operating room just prior to attaching (or connecting) cryoneedle 18 to flow control device 20. Again, evacuated cryoneedles 18 can be attached (or connected) to flow control devices 20 of closed-loop system 10 and 100 without the need for flushing prior to their use.

Figure 3:
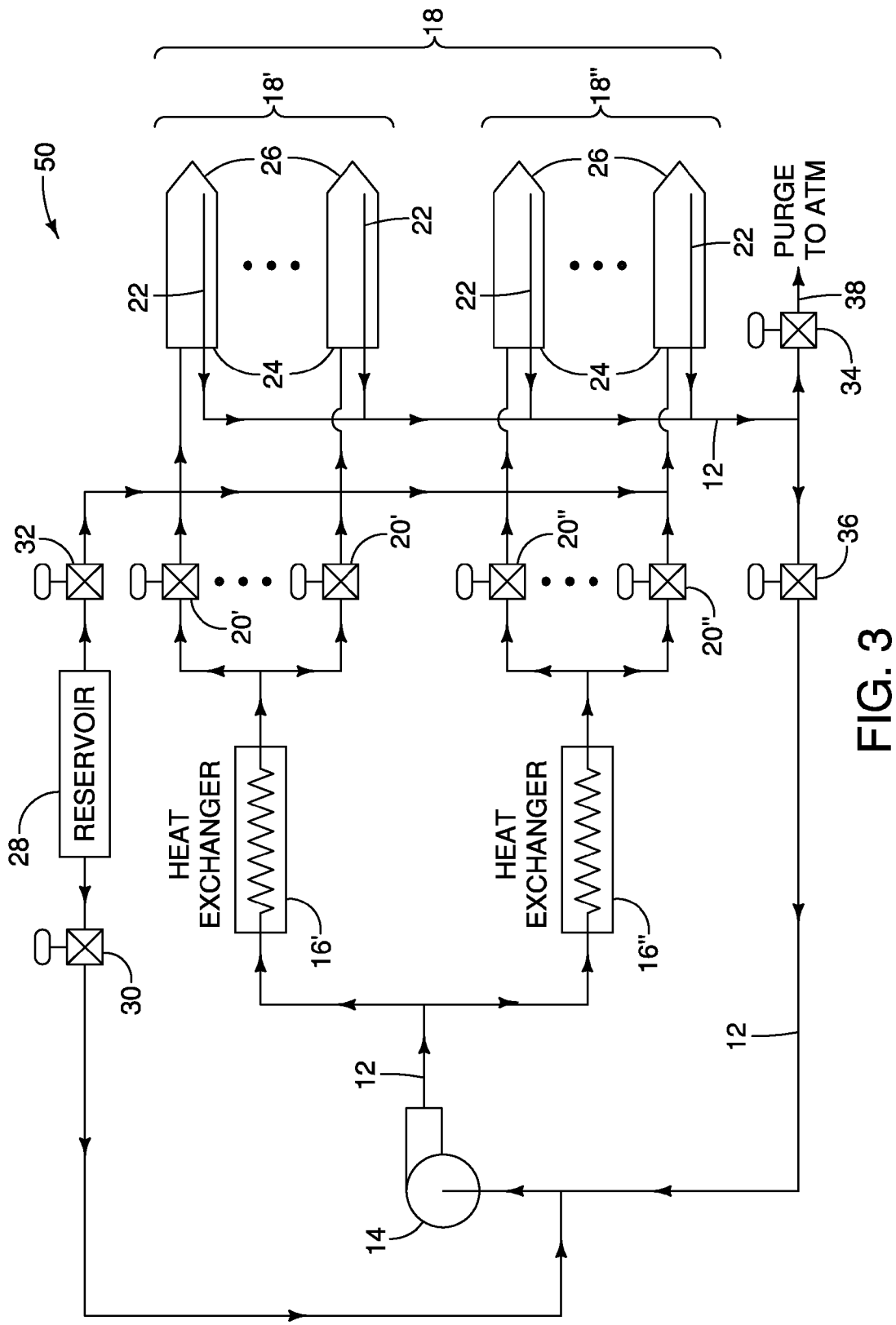
FIG. 3 illustrates another embodiment of a closed-loop system for cryosurgery.

As previously described, heat exchanger 16 is coupled to a heat sink such as a cryogenic dewar and/or a cryocooler. FIG. 1 illustrates an embodiment of system 10 wherein a unitary or single heat sink coupled to unitary or single heat exchanger 16 is sufficient for cooling the cryofluid in flow path 12 to cryogenic temperatures. As an alternative, FIG. 3 illustrates an embodiment of closed-loop system 50 wherein two heat exchangers 16' and 16", each coupled to its respective heat sink, are provided for cooling the cryofluid flowing therethrough to cryogenic temperatures. In the interest of brevity, the following description with reference to FIG. 3 includes only those parameters, i.e., components, operation, etc., of system 50 that differ from the parameters of system 10 as previously described with reference to FIG. 1.

Heat exchangers 16' and 16" are shown downstream of and in parallel fluid communication with pump 14 such that at least a portion of the cryofluid exiting pump 14 enters each heat exchanger 16' and 16". Each heat exchanger 16' and 16" is upstream of and in fluid communication with a respective set or bank of one or more flow control devices 20' and 20" and one or more cryoneedles 18' and 18". As with one or more flow control devices 20, each one of one or more flow control devices 20' and 20" is configured for selectively connecting or disconnecting a respective set or bank of one or more cryoneedles 18' and 18" to flow path 12. Accordingly, each one of one or more flow control devices 20' and 20" is configured to enable or disable the flow of cryofluid between flow path 12 and each one of one or more cryoneedles 18' and 18". The cryofluid exiting each one of one or more cryoneedles 18' and 18" converges or combines into a single flow path to pump 14.

While FIG. 3 shows heat exchangers 16' and 16" in respective fluid communications with one or more flow control devices 20' and 20", this does not always have to be the case. For example, in an alternate embodiment of the closed-loop system, both heat exchangers 16' and 16" are in fluid communication with a single set or bank of flow control devices such as one or more flow control devices 20. As such, the cryofluid exiting each heat exchanger 16' and 16" along respective parallel flow paths is first merged or combined into a single flow path leading to a single set or bank of flow control devices such as one or more flow control devices 20. Accordingly, both heat exchangers 16' and 16" are upstream of and in fluid communication with the single set or bank of flow control devices such as one or more flow control devices 20.

Figure 4:
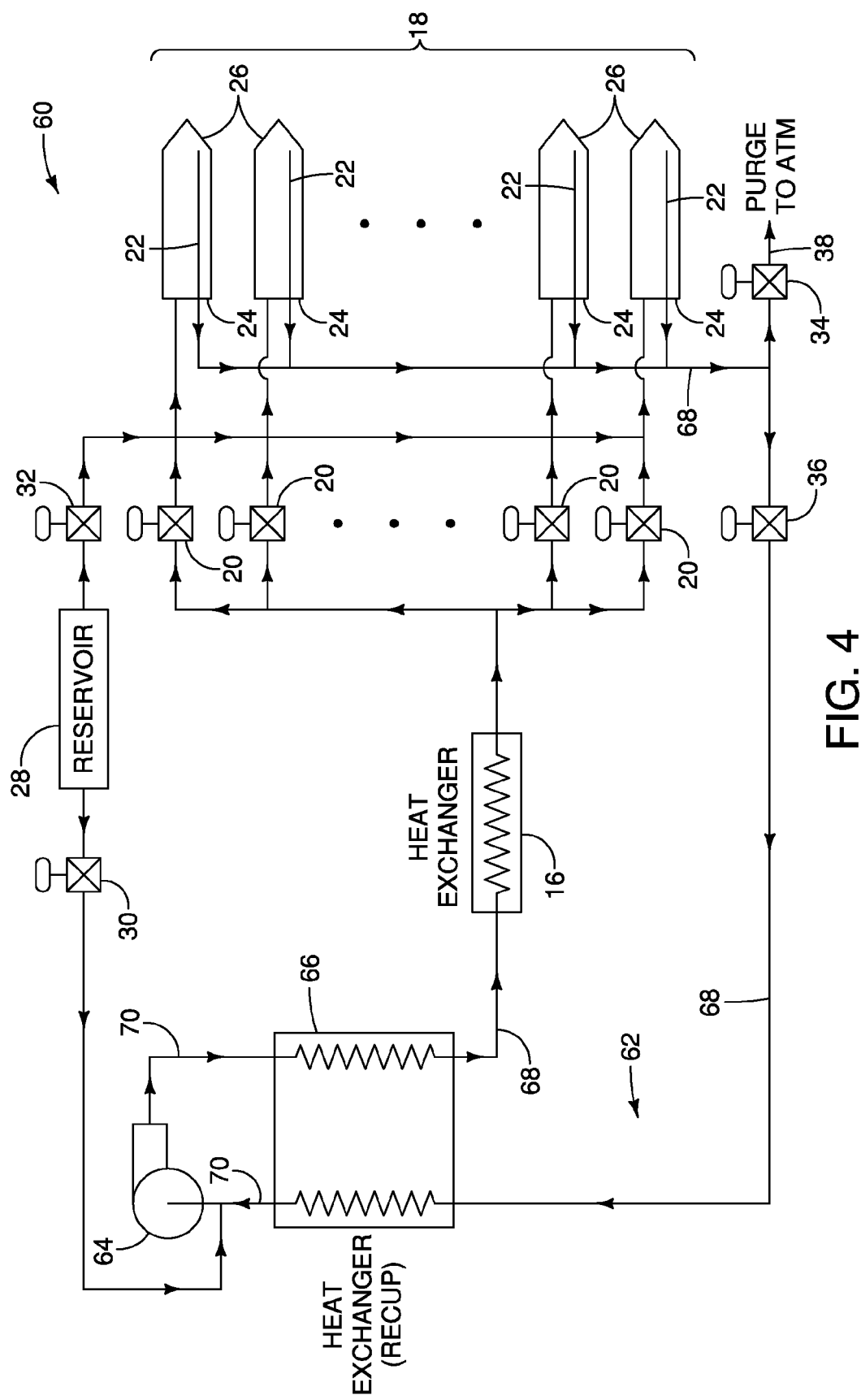
FIG. 4 illustrates yet another embodiment of a closed-loop system for cryosurgery.

As previously described with reference to FIGS. 1 and 3, each heat exchanger 16, 16' and 16" is coupled to a heat sink configured for cooling the cryofluid in flow path 12 from approximately 150° K to approximately 110° K. As such, flow path 12 is considered to be at cryogenic temperatures, and pump 14 and each one of one or more flow control devices 20 are configured for operating with cryofluid having a temperature of less than or equal to approximately 150° K. FIG. 4 illustrates an alternate embodiment of closed-loop system 60 having closed-loop flow path 62 wherein pump 64 is configured for operating at a temperature substantially greater than cryogenic temperatures. In the interest of brevity, the following description with reference to FIG. 4 includes only those parameters, i.e., components, operation, etc., of system 60 that differ from the parameters of systems 10 and 50 as previously described with reference to FIGS. 1 and 3, respectively.

As depicted in FIG. 4, closed-loop flow path 62 includes recuperator 66 both for heating the cryofluid after it exits one or more cryoneedles 18 and before it enters pump 64 and for cooling the cryofluid after it exits pump 64 and before it enters heat exchanger 16. Accordingly, flow path 62 is defined at least partially by first and second sections 68 and 70, respectively, with recuperator 66 therebetween. First section 68 includes at least heat exchanger 16, one or more cryoneedles 18 and one or more flow control devices 20; and second section 70 includes at least pump 64. Heat exchanger 16 is coupled to a heat sink configured for cooling the cryofluid from approximately 150° K to approximately 110° K. Therefore, first section 68 of flow path 62, and the cryofluid therein, will generally be at cryogenic temperatures of less than or equal to approximately 150° K. Recuperator 66 is configured for transferring thermal energy between first and second sections 68 and 70, respectively. More specifically, recuperator 66 extracts thermal energy from the cryofluid flowing from second section 70 to first section 68 and inserts the extracted thermal energy into the cryofluid flowing from first section 68 to second section 70. As such, the temperature of the cryofluid flowing from second section 70 to first section 68 decreases; and the temperature of the cryofluid flowing from first section 68 to second section 70 increases. Therefore, second section 70 of flow path 62, and the cryofluid therein, will generally be at a temperature substantially greater than that of first section 68. Accordingly, pump 64 is configured for operating at temperatures substantially greater than cryogenic temperatures.

In a non-limiting exemplary embodiment, pump 64 is configured for operating at room temperatures. Accordingly, second section 70 and the cryofluid therein will be at a temperature between approximately 285° K and approximately 310° K. In one such embodiment, the thermal energy transferred from second section 70 to first section 68 is about 750 watts, and the cryofluid flowing from first section 68 to second section 70 increases from approximately 150° K to approximately 297° K as it flows through recuperator 66. The temperature of the cryofluid increases by approximately 3° K as it flows through pump 64. Thereafter, the temperature of the cryofluid flowing from second section 70 to first section 68 decreases from approximately 300° K to approximately 157° K as it flows through recuperator 66. It will be apparent to one skilled in the art that the amount of thermal energy transferred between first and second sections 68 and 70, respectively, and the temperature of the cryofluid in each section can be affected by configuring recuperator 66 differently from the described example.

In some embodiments of system 60, pump 64 is a constant flow pump configured to maintain the cryofluid flow rate within a relatively narrow predefined range. In other embodiments of system 60, pump 64 is a variable flow pump configured to accommodate cryofluid flow rates over a relatively wide predefined range.

With reference to FIGS. 1 and 4, it will be apparent to one skilled in the art that one difference between systems 10 and 60 is the exclusion of recuperator 66 from closed-loop flow path 12 of system 10, and the inclusion of recuperator 66 in closed-loop flow path 62 of system 60. It will be evident that systems 10 and 60 are substantially similar in several other aspects. It will also be apparent to one skilled in the art that the systems illustrated in FIGS. 3 and 4 can be integrated or combined to create an alternate embodiment of system 50 or system 60. In essence, the alternate embodiment of system 50 will include recuperator 66 in flow path 12 of system 50. Or, when considered from the point of view of system 60, the alternate embodiment of system 60 will include, as previously described with reference to FIG. 3, heat exchangers 16' and 16" in fluid communication with a set or bank of one or more flow control devices 20' and 20" and one or more cryoneedles 18' and 18".

Figure 5:
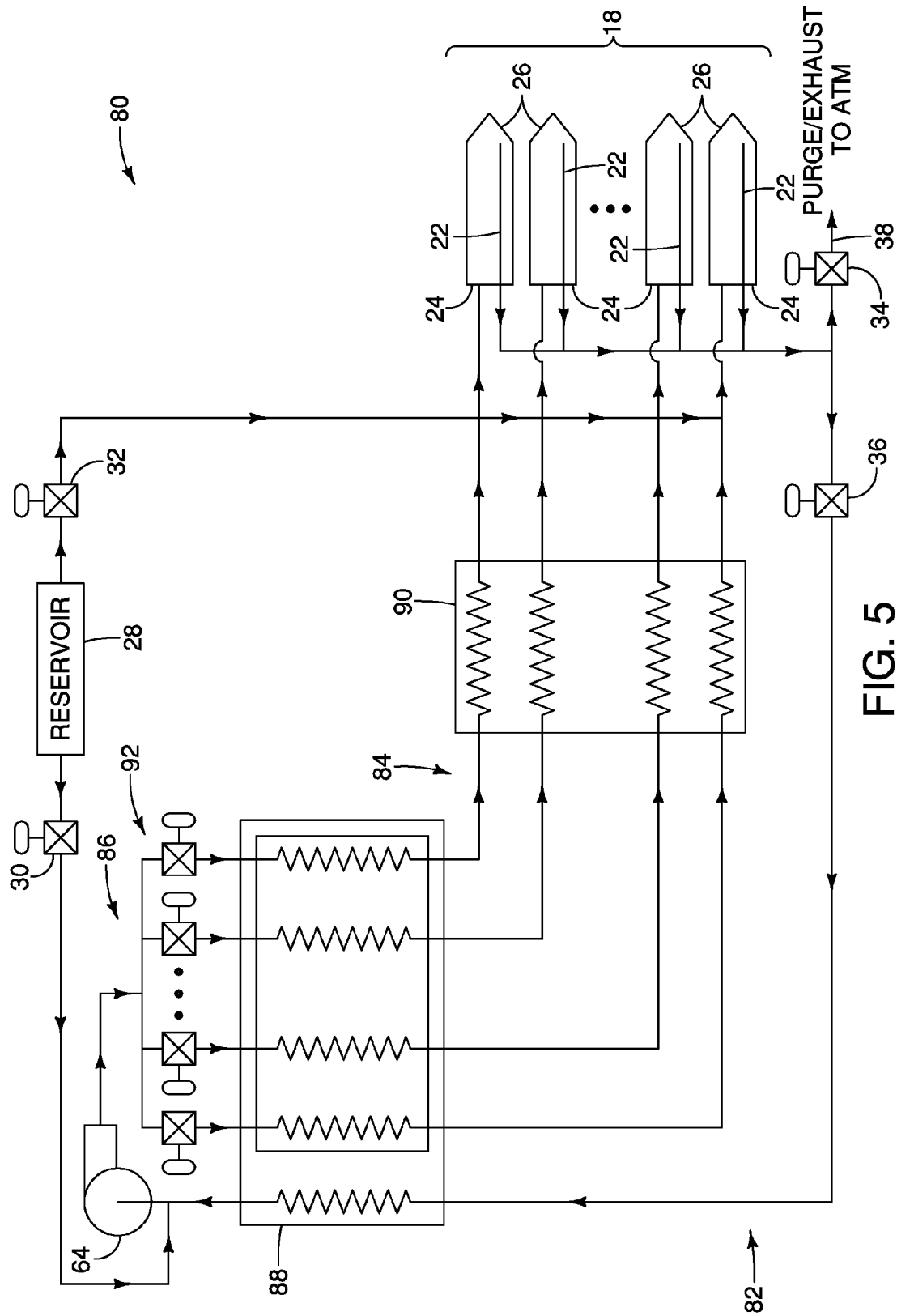
FIG. 5 illustrates an alternate embodiment of a closed-loop system for cryosurgery.

FIG. 5 illustrates an alternate embodiment of closed-loop system 80. In the interest of brevity, the following description with reference to FIG. 5 includes only those parameters, i.e., components, operation, etc., of system 80 that differ from the parameters of systems 10, 50 and 60 as previously described with reference to FIGS. 1, 3 and 4, respectively.

System 80 includes closed-loop flow path 82 defined at least partially by first and second sections 84 and 86, respectively, with recuperator 88 therebetween. First section 84 includes at least heat exchanger 90 and one or more cryoneedles 18; and second section 86 includes at least pump 64 and one or more flow control devices 92. Heat exchanger 90 is coupled to a heat sink configured for cooling the cryofluid from approximately 150° K to approximately 110° K. Therefore, first section 84 of flow path 82, and the cryofluid therein, will generally be at cryogenic temperatures of less than or equal to approximately 150° K. Recuperator 88 is configured for transferring thermal energy between first and second sections 84 and 86, respectively. More specifically, recuperator 88 extracts thermal energy from the cryofluid flowing from second section 86 to first section 84 and inserts the extracted thermal energy into the cryofluid flowing from first section 84 to second section 86. As such, the temperature of the cryofluid flowing from second section 86 to first section 84 decreases; and the temperature of the cryofluid flowing from first section 84 to second section 86 increases. Therefore, second section 86 of flow path 82, and the cryofluid therein, will generally be at a temperature substantially greater than that of first section 84. Accordingly, pump 64 and each one of one or more flow control devices 92 are configured for operating at temperatures substantially greater than cryogenic temperatures. In a non-limiting exemplary embodiment, pump 64 and flow control devices 92 are configured for operating at room temperatures.

As illustrated, the relatively warmer second section 86 includes flow control devices 92 downstream of and in parallel fluid communication with pump 64. Each one of one or more flow control devices 92 is configured for selectively enabling and disabling the flow of cryofluid between flow path 82 and one or more cryoneedles 18. Accordingly, recuperator 88 and heat exchanger 90 are each configured with at least one passage through which the cryofluid flows from at least one flow control device 92 to at least one cryoneedle 18. In other words, each flow path between at least one flow control device 92 and at least one cryoneedle 18 extends through both recuperator 88 and heat exchanger 90. The cryofluid exiting one or more cryoneedles 18 is combined into a single flow path that extends through recuperator 88 to pump 64.

As previously described with reference to closed-loop systems 10, 50, and 60, an alternate embodiment of system 80 includes two or more heat exchangers instead of the single heat exchanger 90 illustrated in FIG. 5. Each one of the two or more heat exchangers will be coupled to a heat sink configured for cooling the cryofluid to cryogenic temperatures.

Although not illustrated in any of FIGS. 1-5, it will be apparent to one skilled in the art that a control system and additional components, plumbing, etc. may be or will be required for operating the one or more closed-loop systems. For example, a control system may be necessary for monitoring the pressures and/or temperatures of the cryofluid at various locations in the closed-loop flow path, regulating the pump, flow control devices, heat sinks (e.g., one or more cryocoolers), the reservoir during pressurization and/or flushing, etc. Additionally or in the alternative, by-pass plumbing may be required for maintaining a constant flow of the cryofluid and/or for regulating the system pressure when only some, and not all, cryoneedles are flow connected to the closed-loop flow path. Furthermore, additional components such as check valves, dryers, etc. may be included in the various embodiments of the closed-loop system.

In view of the foregoing, several alternative combinations and permutations of closed-loop systems 10, 100, 50, 60 and 80 will become apparent to one skilled in the art. All such alternatives and variations are considered as being within the metes and bounds of the claimed invention. For instance, as with system 10 and 100, each one of systems 50, 60 and 80 can be configured for one or more of flushing, conditioning, and/or pre-charging cryoneedles 18 prior to their use in a cryosurgical procedure. Accordingly, as with system 100, alternate embodiments of each one of systems 50, 60 and 80 include flush valve 40 in fluid communication with reservoir 28 and configured for attaching (or connecting) cryoneedle 18 thereto. The procedures for one or more of flushing, conditioning, charging, and/or evacuating one or more cryoneedles for use with each one of systems 50, 60 and 80, and their alternate embodiments, is substantially the same as that described hereinabove with reference to closed-loop systems 10 and 100 illustrated, respectively, in FIGS. 1 and 2.

Various modifications may become apparent based on the above detailed description of certain non-limiting exemplary embodiments without departing from the spirit, scope and intent of the invention. For example, while the described embodiments refer to particular features and/or functions, the invention is considered to also include embodiments having combinations of features and/or functions different from those described. Accordingly, the scope and intent of the invention is intended to embrace all such alternatives, modifications, variations, etc., as may become apparent to one skilled in the art. The metes and bounds of the invention are defined by the appended claims and any and all equivalents thereof.

We claim:

1. A closed-loop system for cryosurgery, comprising
    a closed-loop flow path for a cryofluid at cryogenic temperatures, said closed-loop flow path having a nominal pressure not less than about 9.5 MPa throughout the close-loop flow path and at cryogenic temperatures lower than about 150 Kelvin throughout the closed-loop flow path;
    a pump for circulating and maintaining said cryofluid at the nominal pressure in said closed-loop flow path, the pump being in fluid communication with the closed-loop fow path such that cryofluid flows from and is returned to the pump;
    a heat exchanger coupled to a heat sink in said closed-loop flow path for maintaining said cryofluid at cryogenic temperatures;
    one or more cryoneedles selectively flow connected in said closed-loop flow path, each cryoneedle configured to provide a cryotherapy; and
    one or more flow control devices in said closed-loop flow path, each flow control device configured for selectively flow connecting and flow disconnecting at least one of said one or more cryoneedles with said closed-loop flow path, thereby enabling and disabling, respectively, a flow of said cryofluid at cryogenic temperatures between said closed-loop flow path and said at least one cryoneedle.

2. The system of claim 1, wherein
    said one or more cryoneedles flow connected to said closed-loop flow path are downstream of said heat exchanger and upstream of said pump; and
    said heat exchanger is downstream of said pump.

3. The system of claim 2, wherein said closed-loop flow path is defined at least partially by
    serial fluid communication between said heat exchanger and said pump;
    parallel fluid communication between said heat exchanger and said one or more cryoneedles flow connected to said closed-loop flow path; and
    parallel fluid communication between said pump and said one or more cryoneedles flow connected to said closed-loop flow path.

4. The system of claim 3, wherein said heat exchanger comprises two or more heat exchangers downstream of and in parallel fluid communication with said pump; and
    wherein each one of said two or more heat exchangers is coupled to a heat sink and is upstream of and in parallel fluid communication with one or more cryoneedles flow connected to said closed-loop flow path.

5. The system of claim 1, further comprising a cryofluid reservoir configured for selectively
   adding cryofluid to said closed-loop flow path; and
   flushing each one of said one or more cryoneedles flow connected to said closed-loop flow path.

6. The system of claim 5, wherein each one of said one or more cryoneedles flow connected to said closed-loop flow path is flushed before enabling said flow of said cryofluid therebetween.

7. The system of claim 6, comprising a flush valve in fluid communication with said cryofluid reservoir, said flush valve configured for
   attaching at least one of said one or more cryoneedles thereto; and
   flushing said one or more cryoneedles attached thereto.

8. The system of claim 1, futher comprising a cryofluid reservoir configured for selectively
   pressurizing said closed-loop flow path when a pressure within said closed-loop flow path is less than a predefined minimum pressure; and
   flushing each one of said one or more cryoneedles flow connected to said closed-loop flow path.

9. The system of claim 1, wherein said heat sink is one of a cryocooler and a cryogenic dewar.

10. The system of claim 9, wherein said cryocooler is selected from the group consisting of a Stirling-type cooler, a pulse-tube refrigerator (PTR), a Gifford-McMahon (GM) cooler, and a Joule-Thomson (JT) cooler; and wherein said cryocooler is configured for extracting between approximately 100 Watts and approximately 500 Watts of thermal energy from said cryofluid in said closed-loop flow path and cooling said cryofluid from approximately 150° K to approximately 110° K.

11. The system of claim 1, wherein said pump is operable at cryogenic temperatures and configured for circulating said cryofluid in said closed-loop system at a flow rate ranging between approximately 0.1 liters/minute and approximately 0.8 liters/minute and at a nominal pressure of approximately 10 MPa.

12. The system of claim 1, wherein each one of said one or more flow control devices is operable at cryogenic temperatures.

13. The system of claim 1, wherein said closed-loop flow path is hermetically sealed.

14. The system of claim 1, wherein said nominal pressure has a variance of approximately ±0.5 MPa.

15. The system of claim 1, wherein each one of said one or more cryoneedles is pre-charged with said cryofluid.

16. The system of claim 15, wherein said one or more pre-charged cryoneedles is attached to at least one of said one or more flow control devices during cryosurgery.

17. The system of claim 1, wherein the cryofluid is supplied by a reservoir, the cryofluid circulating though the closed-loop flow path as a compressed gas, the compressed gas being one of argon or nitrogen at high pressure.

18. The system of claim 17, wherein the cryofluid is at an approximately constant pressure in the closed-loop flow path.

19. A closed-loop system for cryosurgery, comprising
   a closed-loop flow path for a cryofluid at cryogenic temperatures, said closed-loop flow path having a nominal pressure not less than about 9.5 MPa throughout the closed-loop flow path and including a first section and a second section;
   a pump positioned in the second section of the closed-loop flow path for circulating said cryofluid in said closed-loop flow path, the pump being in fluid communication with the closed-loop flow path such that cryofluid flows from and is returned to the pump;
   a heat exchanger coupled to a heat sink and positioned in the first section of the closed-loop flow path for cooling said cryofluid in the first section of the closed-loop flow path to cryogenic temperatures;
   a recuperator in said closed-loop flow path, the recuperator positioned between the first section and the second section, said recuperator configured for transferring thermal energy between said cryofluid in said second section and said cryofluid in said first section, the second section having an operating temperature substantially greater than cryogenic temperatures, such that the recuperator precools the cryfluid flwowing from the pump in the second section toward the heat exchanger in the first section; and
   one or more cryoneedles positioned in the first section of the closed-loop flow path, each cryoneedle configured to provide a cryotherapy.

20. The system of claim 19, wherein a change in temperature of said cryofluid in said first section is substantially equal to a change in temperature of said cryofluid in said second section.

21. The system of claim 19, wherein said heat exchanger comprises two or more heat exchangers, each coupled to a heat sink and configured for cooling said cryofluid in said closed-loop flow path to cryogenic temperatures.

22. The system of claim 21, wherein the two or more heat exchangers are positioned downstream of said second section; and wherein each one of said tow or more heat exchangers is upstream of and in parallel fluid communication with one or more cryoneedles flow connected to said closed-loop path.

23. The system of claim 19, comprising a cryofluid reservoir configured for selectively
   adding cryofluid to said closed-loop flow path; and
   flushing each one of said one or more cryoneedles flow connected to said closed-loop flow path.

24. The system of claim 19, wherein said heat sink is one of a cryocooler and a cryogenic dewar.

25. The system of claim 24, wherein said cryocooler is selected from the group consisting of a Stirling-type cooler, a pulse-tube refrigerator (PTR), a Gifford-McMahon (GM) cooler, and a Joule-Thomson (JT) cooler; and wherein said cryocooler is configured for extracting between approximately 100 Watts and approximately 500 Watts of thermal energy from said cryofluid in said closed-loop flow path and cooling said cryofluid from approximately 150° K to approximately 110° K.

26. The system of claim 19, wherein said pump is configured for circulating said cryofluid in said closed-loop system at a flow rate ranging between approximately 0.1 liters/minute and approximately 0.1 liters/minute and at a nominal pressure of approximately 10 MPa.

27. The system of claim 19, further comprising one or more flow control devices positioned in the second section of the closed-loop flow path, each flow control device configured for selectively enableing and disabling a flow of said cryofluid at cryogenic temperatures between said closed-loop flow path and one or more of the cryoneedles.

28. A closed-loop system for cryosurgery, comprising
   a closed-loop flow path for a cryofluid at cryogenic temperatures, said closed-loop flow path having a nominal pressure not less than about 9.5 MPa throughout the closed-loop flow path and being at cryogenic temperatures lower than about 150 Kelvin throughout the closed-loop flow path;

a pump for circulating said cryofluid in said closed-loop flow path the pump being in fluid communication with the closed-loop flow path such that cryofluid flows from and is returned to the pump;

a heat exchanger coupled to a heat sink and in said closed-loop flow path for cooling said cryofluid to cryogenic temperatures, said heat sink is one of a cryocooler and a cryogenic dewar holding a quantity of a cryogen, said heat sink is configured for extracting between approximately 100 Watts and approximately 500 Watts of thermal energy from said cryofluid in said closed-loop flow path one or more cryoneedles selectively flow connected in said closed-loop flow path, each cryoneedle configured to provide a cryotherapy; and one or more flow control devices in said closed-loop flow path, each flow control device configured for selectively flow connecting and flow disconnecting at least one of said one or more cryoneedles with said closed-loop flow path, thereby enabling and disabling, respectively, a flow of said cryofluid at cryogenic temperatures between said closed-loop flow path and said at least one cryoneedle.

29. The closed-loop system of claim 28, wherein the heat sink is a cryogenic dewar holding a quantity of a cryogen configured for extracting approximately 500 Watts of thermal energy from the cryofluid.

30. The closed loop system of claim 28, wherein the cryogen is liquid nitrogen.

* * * * *

UNITED STATES PATENT AND TRADEMARK OFFICE
CERTIFICATE OF CORRECTION

PATENT NO. : 9,078,733 B2  
APPLICATION NO. : 13/569822  
DATED : July 14, 2015  
INVENTOR(S) : Satish Ramadhyani et al.

Page 1 of 1

It is certified that error appears in the above-identified patent and that said Letters Patent is hereby corrected as shown below:

Claim 19, Column 12, line 16, please replace "cryfluid flwowing" with --cryofluid flowing--

Claim 26, Column 12, line 56, please replace "0.1" with --0.8--

Claim 27, Column 12, line 61, please replace "enableing" with --enabling--

Signed and Sealed this  
Twelfth Day of January, 2016

Michelle K. Lee  
*Director of the United States Patent and Trademark Office*